(12) United States Patent
Kourai et al.

(10) Patent No.: US 6,436,890 B1
(45) Date of Patent: Aug. 20, 2002

(54) ANTIMICROBIAL DETERGENT COMPOSITION

(75) Inventors: Hiroki Kourai; Takuya Maeda, both of Tokushima; Munehiro Yoshida, Takamatsu; Kensei Kunikata; Kouji Wada, both of Kagawa-ken, all of (JP)

(73) Assignee: Inui Corporation, Osaka (JP)

( * ) Notice: Subject to any disclaimer, the term of this patent is extended or adjusted under 35 U.S.C. 154(b) by 107 days.

(21) Appl. No.: 09/684,615

(22) Filed: Oct. 10, 2000

(30) Foreign Application Priority Data

Oct. 12, 1999 (JP) ............................................. 11-289417

(51) Int. Cl.$^7$ ............................. C11D 3/48; C11D 1/62
(52) U.S. Cl. ....................... 510/384; 510/130; 510/131; 510/382; 510/391; 510/504
(58) Field of Search ................................. 510/130, 131, 510/382, 384, 391, 504

(56) References Cited

FOREIGN PATENT DOCUMENTS

| JP | 6-321902 | * | 11/1994 |
| JP | 8-301703 | * | 11/1996 |
| JP | 9-110692 | * | 4/1997 |
| JP | 10-095773 | * | 4/1998 |
| JP | 10-287566 | * | 10/1998 |

* cited by examiner

Primary Examiner—Charles Boyer
(74) Attorney, Agent, or Firm—Sherman & Shalloway

(57) ABSTRACT

The present invention provides an antimicrobial detergent composition containing, as an antimicrobial agent, a bis-quaternary ammonium compound of the general formula

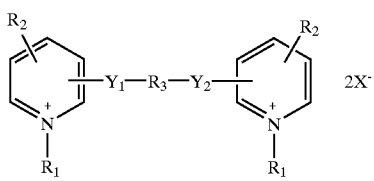

(I)

wherein the two $R_1$ may be the same or different and each represents an alkyl group of 1 to 18 carbon atoms or an alkenyl group of 3 to 18 carbon atoms; the two $R_2$ may be the same or different and each represents a hydrogen atom, a halogen atom, a hydroxyl group, an amino group, an alkyl group of 1 to 6 carbon atoms or an alkoxy group of 1 to 3 carbon atoms; $R_3$ represents an alkylene group of 1 to 18 carbon atoms, an alkenylene group of 3 to 18 carbon atoms or a phenylene or xylylene group which may optionally be substituted by an alkyl group of 1 to 18 carbon atoms, an alkoxy group of 1 to 6 carbon atoms or an alkoxycarbonyl group of 2 to 6 carbon atoms; $Y_1$ represents —NHCO—, —CONH—, —NHCS—, —COO—, —COS—, —O— or —S—; $Y_2$ represents —CONH—, —NHCO—, —CSNH—, —OOC—, —SOC—, —O— or —S—; and X represents an anion.

6 Claims, No Drawings

ANTIMICROBIAL DETERGENT COMPOSITION

The present invention relates to antimicrobial detergent compositions which can be used for the purpose of removal of microorganism and deodorization of washings and sterilization and antibacterialization etc. in food factories, hospitals etc. and more specifically relates to antimicrobial detergent compositions which can be used favorably as detergents and softeners used for washing, detergents for cleaning, detergents used for walls, floors etc. of food factories, hospitals etc.

Clothes, bed sheets etc. used in the clinical spots used to be contaminated with blood, fluid, fat etc. and further with pathogens, viruses etc. For these clothes, bed sheets etc. detergents containing bactericide should be used to conduct not only washing but also such treatments as sterilization, antibacterialization, removal of microorganism, deodorization etc. Moreover, in cleaning, a bactericide is used usually with detergents to prevent clothes from contamination and keep them in a hygienic condition.

Recently, perhaps from cleanliness-oriented tendency, removal of microorganism and odor of clothes, bed sheets etc. are conducted also at general household together with washing and therefore detergents, softeners etc. containing bactericide appear on the market. Among these antimicrobial agents for washing, however, there are antimicrobial agents which appear adaptation of bacteria when used for longer period of time and lose effects of removal of microorganism, deodorization etc.

Infection of drug-resistant bacteria such as MRSA (Methicillin-resistant *Staphylococcus aureus*) to weak inpatients in hospitals has become a big social problem and it is desired to use detergents containing bactericides, which do not produce drug-resistant bacteria, as detergents to be used for walls, floors etc. Moreover, the existence of not only drug-resistant bacteria but also bacteria themselves matters in food factories and therefore there are desired highly safe antimicrobial agents which not only produce no drug-resistant bacteria but also have a wide antimicrobial activity spectrum.

The object of the present invention is to provide a highly safe antimicrobial agent which not only produces no drug-resistant bacteria but also has a wide antimicrobial activity spectrum even in case it is used for a longer period of time contained in detergents, softeners, detergents for cleaning and detergents used for walls, floor etc. of food factories, hospitals etc.

The present inventors have been intensively studying to solve the above-mentioned problem. As a result, this time, they found that bis-quarternary ammonium compounds represented by the following general formula (I) are suitable to be used for a longer period of time contained in detergents, softeners, detergents for cleaning and detergents used for walls, floor etc. of food factories, hospitals etc. (in the present specification they are collectively called as "detergent composition"), because they are highly safe to human body and natural environment, have a wide antimicrobial activity spectrum, produce no drug-resistant bacteria even in case of use for a longer period of time, and show effects against MRSA at a low concentration and completed the present invention.

Thus, according to the present invention, there is provided an antimicrobial detergent composition characterized by containing, as an antimicrobial agent, at least one bis-quaternary ammonium compound of the general formula

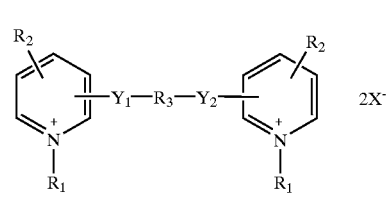

wherein the two $R_1$ may be the same or different and each represent an alkyl group of 1 to 18 carbon atoms or an alkenyl group of 3 to 18 carbon atoms; the two $R_2$ may be the same or different and each represent a hydrogen atom, a halogen atom, a hydroxyl group, an amino group, an alkyl group of 1 to 6 carbon atoms or an alkoxy group of 1 to 3 carbon atoms; $R_3$ represents an alkylene group of 1 to 18 carbon atoms, an alkenylene group of 3 to 18 carbon atoms or a phenylene or xylylene group which may optionally be substituted by an alkyl group of 1 to 18 carbon atoms, an alkoxy group of 1 to 6 carbon atoms or an alkoxycarbonyl group of 2 to 6 carbon atoms; $Y_1$ represents —NHCO—, —CONH—, —NHCS—, —COO—, —COS—, —O— or —S—; $Y_2$ represents —CONH—, —NHCO—, —CSNH—, —OOC—, —SOC—, —O— or —S—; and X represents anions.

The antimicrobial (i.e., antibacterial or antifungal) detergent compositions of the present invention will be more specifically described hereinbelow.

As used herein, the term "alkyl group" denotes a straight-chain or branched alkyl group, and examples thereof include methyl, ethyl propyl, isopropyl, butyl, isobutyl, sec-butyl pentyl, isopentyl, sec-pentyl, hexyl, heptyl, octyl, 2-ethylhexyl, nonyl, decyl isodecyl, dodecyl, tetradecyl, hexadecyl and octadecyl etc. From the viewpoint of antibacterial power, the alkyl groups represented by $R_1$ are preferably ones having 8 or more carbon atoms.

The term "alkenyl group" denotes a straight-chain or branched alkenyl group, and examples thereof include allyl, methallyl, pentenyl hexenyl, heptenyl, octenyl, nonenyl, decenyl, undecenyl, dodecenyl, tetradecenyl, hexadecenyl and octadecenyl, etc.

The term "alkoxy group" denotes an alkyloxy group in which the alkyl moiety has the above-described meaning, and examples thereof include methoxy, ethoxy, propoxy, isopropoxy, butoxy, isobutoxy, sec- butoxy and tert- butoxy.

The term "alkylene group" preferably denotes a group of the formula —(CH$_2$)$_n$—. In this formula, n is preferably in the range of 2 to 18 and more preferably 3 to 8.

The term "alkenylene group" comprehends, for example, —CH=CH—, —CH=CH—CH$_2$— and —CH$_2$—CH=CH—CH$_2$—.

The term "alkoxycarbonyl group" denotes an alkyloxycarbonyl group in which the alkyl moiety has the above-described meaning, and examples thereof include methoxycarbonyl and ethoxycarbonyl.

The term "halogen atom" comprehends fluorine, chlorine, bromine and iodine.

The term "anion" comprehends inorganic anions such as halogen ions (e.g., Cl$^-$, Br$^-$ and I$^-$) and nitrate ion (NO$_3^-$); and organic acid anions such as acetate ion (CH$_3$COO$^-$) and propionate ion (C$_2$H$_5$COO$^-$).

Among the compounds represented by the above formula (I), a preferred group of compounds are those of formula (I) in which the two $R_1$ may be the same or different, and each represents an alkyl group of 8 to 18 carbon atoms; the two $R_2$ may be the same or different, and each represents a hydrogen atom or a chlorine atom; $R_3$ represents an alkylene group of 3 to 8 carbon atoms, a phenylene group or a xylylene group; $Y_1$ represents —NHCO—, —CONH—, —COO— or —S—; $Y_2$ represents —CONH—, —NHCO—, —OOC— or —S—; and X represents a halogen ion or an acetate ion.

Specific examples of the compounds of the above formula (I) used as antimicrobial agents in the composition of the present invention are as follows:

N,N'-Hexamethylenebis(4-carbamoyl-1-decylpyridinium bromide) ("Dimer 38"; manufactured by INUI CORPORATION), N,N'-hexamethylenebis(4-carbamoyl-1-decylpyridinium acetate) ("Dimer 38A"; manufactured by INUI CORPORATION), 4,4'-(tetramethylenedicarbonyldiamino)bis(1-decylpyridinium bromide) ("Dimer 136"; manufactured by INUI CORPORATION 4,4'-(tetramethylenedicarbonyldiamino)bis(1-decylpyridinium acetate) ("Dimer 136A"; manufactured by INUI CORPORATION), 1,4-tetramethylenebis(4-carbamoyl-1-hexadecylpyridinium bromide), 1,6-hexamethylenebis(3-carbamoyl-1-dodecylpyridinium bromide), 1,8-octamethylenebis(3-carbamoyl-1-tetradecylpyridinium bromide), 3,3'-(1,3-trimethylenedicarbonyldiamino)bis(1-decylpyridinium bromide), 4,4'-(p-xylyldithio)bis(1-octylpyridinium iodide), 3,3'-(m-xylyldithio)bis(1-tetradecylpyridinium bromide), N, N'-(p-phenylene)bis(4-carbamoyl-1-octylpyridinium bromide), N,N'-(m-phenylene)bis(3-carbamoyl-1-dodecylpyridinium bromide), 4,4'-(p-phthalamido)bis(1-octylpyridinium bromide), 3,3'-(m-phthalamido)bis(1-octadecylpyridinium iodide), 4,4'-(1,8-octamethylenedioxy)bis(1-dodecylpyridinium bromide), 3,3'-(1,6-hexamethylenedioxy)bis(1-hexadecylpyridinium bromide), 4,4'-(1,6-hexamethylenedioxydicarbonyl)bis(1-octylpyridinium bromide), 3,3'-(1,4-tetramethylenedioxydicarbonyl)bis(1-dodecylpyridinium bromide), 4,4'-(1,4-tetramethylenedicarbonyldioxy)bis(1-octylpyridinium bromide), 3,3'-(p-phthaloyldioxy)bis(1-decylpyridinium chloride), 4,4'-(1,8-octamethylenedicarbonyldithioxy)bis(1-octadecylpyridinium bromide) and 3,3'-(m-phthaloyldithioxy)bis(1-decylpyridinium iodide).

The compounds of the above formula (I) are disclosed, for example, in the publications of Japanese Laid-Open Patent Publication (KOKAI) Nos. 1106921/'97, 957731/'98, 287566/'98, P2000-95763A and P2000-136185A, all of which were filed in the name of the present applicant or assignee, or may be prepared according to the processes described in these publications or specifications.

The compounds of the above formula (I) are extremely safe with low toxicity and little skin irritation.

The compounds of the above formula (I) can be used each singly or in combination of 2 kinds or more for detergents, softeners, detergents for cleaning and detergents used for walls, floor etc. of food factories, hospitals etc. or can be used together with other agents such as bactericides.

The antimicrobial detergent compositions of the present invention can be prepared in the entirely same procedure as usual detergent compositions, except compounding the compounds of the above formula (I) in the above detergent compositions. The mixed amount in the detergent composition varies according to the application purposes of the final detergent composition, kinds of antimicrobial agents etc. Generally, however, it is preferable in the range of 0.1–50% by weight, particularly 0.5–35% by weight, and more particularly 1–20% by weight, based upon the weight of the composition.

The detergents, in which the compounds of the above formula (I) can be mixed, are solid or liquid compositions comprising soap or other surfactants and containing as auxiliary components builder, foam-forming agent, fluorescent brightening agent, solvent, perfume etc. and include heavy duty detergent mainly used for cleaning of clothes, light duty detergent mainly used for kitchen, housing, shampoo etc.

As surfactants there can be used, for example, nonionic surfactants of ethylene oxide type, alkylphenol type and pluronic type, etc.

The antimicrobial detergent compositions of the present invention have excellent bactericidal, antimicrobial, bacteria-removal and/or deodoring effects and produce no drug-resistant bacteria even on using for longer period of time and therefore can be widely used, for example, for cleaning of clothes and other textile products, for domestic detergents, for cleaning within the facilities such as food factories, hospitals etc.

TEST EXAMPLE 1

Test for adaptation of bacterium to N,N'-hexamethylene-bis (4-carbamoyl-1-decylpyridinium acetate) ("Dimer 38A" manufactured by INUI CORPORATION) and cetylpyridinium chloride (CPC), a commercial product, was conducted by using 4 kinds of bacteria (*Pseudomonas aeruginosa* ATCC 10145, *Escherichia coli*K12 3110, *Bacillus subtilis* ATCC 6633 and *Staphylococcus aureus* IFO 12732). L-broth (5 ml) was inoculated with each bacteria and, after incubation at 37° C. for 18 hours, the MIC (minimum inhibitory concentration) was measured according to the Nutrient Broth liquid medium dilution method. Then MIC was measured again after the number of bacteria was adjusted to about $10^6$ cells/ml by using a bacteria suspension at a lower concentration than the minimum inhibitory concentration (MIC) at the MIC judgement (a bacteria suspension with the highest drug concentration at which the proliferation of bacteria is confirmed). The procedure was repeated 7 times and MIC value at each procedure was recorded to confirm, if drug-resistant bacteria appeared. The results are shown in the following Table 1.

TABLE 1

| Bacteria | Drug | MIC (ppm) | | | | | | |
|---|---|---|---|---|---|---|---|---|
| | | 1 | 2 | 3 | 4 | 5 | 6 | 7 |
| *Pseudomonas aeruginosa* | Dimer 38A | 3.1 | 3.1 | 6.3 | 6.3 | 6.3 | 6.3 | 3.1 |
| ATCC 10145 | CPC | 76.9 | 96.1 | 150 | 192 | 240 | 307 | 384 |
| *Escherichia coli* | Dimer 38A | 1.6 | 0.8 | 0.8 | 0.8 | 1.6 | 1.6 | 1.6 |
| K12W3110 | CPC | 24.6 | 30.7 | 38.3 | 38.3 | 46.2 | 49.2 | 49.2 |
| *Bacillus subtilis* | Dimer 38A | 0.8 | 0.2 | 0.4 | 0.2 | 0.4 | 0.4 | 0.4 |
| ATCC 6633 | CPC | 3.8 | 3.1 | 3.8 | 6.0 | 6.2 | 7.7 | 9.6 |
| *Staphylococcus aureus* | Dimer 38A | 0.1 | 0.01 | 0.05 | 0.01 | 0.1 | 0.1 | 0.05 |
| IFO 12732 | CPC | 0.2 | 0.3 | 0.4 | 0.4 | 0.9 | 1.5 | 2.4 |

It is evident from the above Table 1 that MIC values to all 4 kinds of bacteria increased parallel to the number of procedures with CPC, namely, drug-resistant bacteria appeared. On the contrary, it was found that MIC value remained almost the same as the initial value after 7 repetitions of procedures and no adaptation of bacteria occurred.

TEST EXAMPLE 2

Antimicrobial power against MRSA (Methicillin-resistant *Staphylococcus aureus*) of N,N'-hexamethylenebis (4-carbamoyl-1-decylpyridinium bromide) ("Dimer 38" manufactured by INUI CORPORATION) and 4,4'-(tetramethylenecarbonyldiamino)bis(1-decyl-pyridinium bromide) ("Dimer 136" manufactured by INUI CORPORATION). L-broth (5 ml) was inoculated with *Staphylococcus aureus* JC1 and, after incubation at 37° C. for 18 hours, the MIC (minimum inhibitory concentration) of Dimer 38 and Dimer 136 was measured according to the Nutrient Broth liquid medium dilution method. The results are shown in the following Table 2.

TABLE 2

| | MIC (ppm) | |
|---|---|---|
| | Dimer 38 | Dimer 136 |
| *Staphylococcus aureus* JCI (MRSA) | 0.2 | 0.6 |

It is evident from the above Table 2 that Dimer 38 and Dimer 136 demonstrate an antimicrobial activity against MRSA, a drug-resistant bacteria at a low concentration.

EXAMPLE 1

Two kinds of detergents [A] and [B] were obtained by sufficiently stirring and mixing each component at the compounding composition (% by weight) shown in the following Table 3.

TABLE 3

| Component | Detergent [A] | Detergent [B] |
|---|---|---|
| Compounding composition (% by weight) | | |
| Dimer 38A | 2.0 | 2.0 |
| Polyoxyethylene lauryl ether | 20.0 | 20.0 |
| Coconut oil fatty acid diethanol amide | 5.0 | — |
| Lauric acid diethanol amide | — | 5.0 |
| ETDA 2Na | 2.0 | — |
| Citric acid | — | 2.0 |

TABLE 3-continued

| Component | Detergent [A] | Detergent [B] |
|---|---|---|
| Ethanol/propylene glycol | 4.0 | 4.0 |
| Water | 67.0 | 67.0 |

Bactericidal effect of each of the above detergent was confirmed in the following procedure. A bacteria suspension of about $10^6$ cells/ml of the viable cell count was obtained by suspending in sterile water the bacteria grown by pre-incubation at 35° C. for 20 hours of NA medium which was inoculated with *Eselerichia coli* IFO 3972 (*E. coli*). 0.1 Ml of the bacteria suspension was added to 9.9 ml of each diluted solution of the detergent[A] and detergent[B] shown in the above Table 3, diluted at 1000-fold by using sterile water, and well mixed to prepare test water. At the lapse of time of 5 minutes, 30 minutes and 60 minutes after maintaining these test waters at room temperature, 1 ml of each test water was taken and immediately mixed with each 9 ml of SCDLP medium, and the viable cell count in the diluted liquid was measured. The results were shown in the following Table 4.

TABLE 4

| | Viable cell count (cells/ml) | | | |
|---|---|---|---|---|
| Detergent | Initial cell number | After 5 minutes | After 30 minutes | After 60 minutes |
| Detergent [A] | $1.3 \times 10^6$ | <10 | <10 | <10 |
| Detergent [A] | | <10 | <10 | <10 |

It is evident from the above Table 4 that the detergent[A] and detergent[B] demonstrate bactericidal activity.

EXAMPLE 2

Effect of removal of microorganism was confirmed in case of washing a chopping board for cooking with each of the same detergents [A] and [B] as Example 1. After 3 places of about 3×3 $cm^2$ area parts on the surface of a chopping board were smeared with 0.1 ml of the same *E. coli* suspension as prepared in Example 1 and dried, each of the above detergents [A] and [B], diluted at 1000-fold by using sterile water, was sprayed from a distance of about 15 cm above said area part each 3 times by using a sprayer. (Spraying amount of detergent at one spraying was about 0.5 ml.) Then after keeping the chopping board at room temperature for 5 minutes, 30 minutes and 60 minutes, the part, which was smeared with the bacteria suspension and dried, was carefully wiped off with a sterile gauze. The gauze was washed out with 10 ml of SCDLP medium and the viable cell count in 1 ml of the washing was measured by agar plate incubation method. Three specimens were tested for each sample and viable cell count was calculated as the average value of 3 specimens. The results are shown in the following Table 5.

TABLE 5

| Sprayed detergent | Initial cell number (cells/ml) | Viable cell count in washing (cells/ml) | | | |
|---|---|---|---|---|---|
| | | Control* | After 5 minutes | After 30 minutes | After 60 minutes |
| Detergent [A] | 1.3 × 10⁶ | 5.0 × 10⁴ | <10 | <10 | <10 |
| Detergent [B] | | | <10 | <10 | <10 |

*Control: Chopping board without spraying detergent

It is evident from the above Table 5 that each of the detergent[A] and detergent[B] can remove bacteria from the chopping board by spraying.

EXAMPLE 3

Antimicrobial effect obtained when clothes were treated with a softener containing Dimer 38A (5% aqueous solution) was examined. Sample cloth was prepared by cutting about 3×3 cm² size out of a textile after softening by a general process and dried at 80° C. by using a softener prepared by adding Dimer 38A (5% aqueous solution) to a commercially available softener ("Bounce" manufactured by The Procter & Gamble Inc.) so that its concentration becomes 1%. On the other hand, NA medium was inoculated with *Staphylococcus aureus*IFO 12732 and pre-incubated at 35° C. for 20 hours to grow bacteria, which were suspended with 1/500 NB medium to obtain a bacteria suspension of about 10⁶ cells/ml viable cell-count. After a sample cloth was inoculated with 0.1 ml of the bacteria suspension and placed in a sterile dish, it was incubated at 35° C. for 24 hours. After incubation, the sample cloth was washed out with 10 ml of SCDLP medium and the viable cell count in 1 ml of the washing was measured by agar plate incubation method. Three specimens were tested for each sample and the viable cell count was calculated as the average value of 3 specimens. The results are shown in the following Table 6.

TABLE 6

| Sample | Viable cell count (cells/ml) |
|---|---|
| Dimer 38A (5% aqueous solution) + softener + textile | <10 |
| Softener + textile (control) | 6.2 × 10⁵ |
| Initial cell number | 3.4 × 10⁶ |

It is evident from the above Table 6 that an antimicrobial effect can be given to clothes by treating the clothes with a softener containing Dimer 38A (5% aqueous solution)

EXAMPLE 4

Effect of removal of microorganism was examined in case a kitchen table was wiped with a detergent for kitchen containing Dimer 38A (5% aqueous solution). A 20×20 cm² area part of a kitchen table was wiped with a sterilized gauze (5×5 cm²) impregnated with 5 ml of a commercially available detergent for kitchen ("Joy" manufactured by The Procter & Gamble Inc.), to which Dimer 38A (5% aqueous solution) was added so that its concentration becomes 1%. After wiping off the detergent with a new, sterilized, dry gauze, the wiped-out part was stamped by using 3 specimens of stamp medium (SCDLP agar). After incubation at 30° C. for 2 days, the number of bacteria colonies was measured and judged according to the following standard. The results are shown in the following Table 7.

○: No colony exists on the agar medium.
Δ: 1–10 colonies exist on the agar medium.
X: More than 10 colonies exist on the agar medium.

TABLE 7

| Sample | Microorganism-removing effect | | |
|---|---|---|---|
| | 1 | 2 | 3 |
| Dimer 38A (5% aqueous solution) + detergent for kitchen | ○ | ○ | Δ |
| Detergent for kitchen, (control) | × | × | × |

It is evident from the above Table 7 that a microorganism removing effect can be obtained by wiping a kitchen table with a detergent for kitchen to which Dimer 38A (5% aqueous solution) was added.

What is claimed is:

1. An antimicrobial detergent composition characterized by containing, as an antimicrobial agent, a bis-quaternary ammonium compound of the general formula

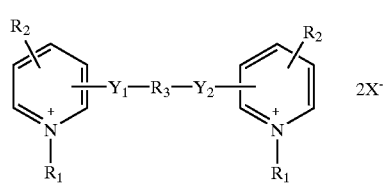

(I)

wherein the two $R_1$ may be the same or different, and each represents an alkyl group of 1 to 18 carbon atoms or an alkenyl group of 3 to 18 carbon atoms; the two $R_2$ may be the same or different, and each represents a hydrogen atom, a halogen atom, a hydroxyl group, an amino group, an alkyl group of 1 to 6 carbon atoms, or an alkoxy group of 1 to 3 carbon atoms; $R_3$ represents an alkylene group of 1 to 18 carbon atoms, an alkenylene group of 3 to 18 carbon atoms, or a phenylene or xylylene group which may optionally be substituted by an alkyl group of 1 to 18 carbon atoms, an alkoxy group of 1 to 6 carbon atoms, or an alkoxycarbonyl group of 2 to 6 carbon atoms; $Y_1$ represents —NHCO—, —CONH—, —NHCS—, —COO—, —COS—, —O— or —S—; $Y_2$ represents —CONH—, —NHCO—, —CSNH—, —OOC—, —SOC—, —O— or —S—; and X represents an anion.

2. The detergent composition of claim 1 wherein, in formula (I), the two $R_1$ may be the same or different, and each represents an alkyl group of 8 to 18 carbon atoms; the two $R_2$ may be the same or different, and each represents a hydrogen atom or a chlorine atom; $R_3$ represents an alkylene group of 3 to 8 carbon atoms, a phenylene group or a xylylene group; $Y_1$ represents —NHCO—, —CONH—, —COO— or —S—; $Y_2$ represents —CONH—, —NHCO—, —OOC— or —S—; and X represents a halogen ion or an acetate ion.

3. The detergent composition of claim 1 wherein the compound of formula (I) is selected from the group consisting of N,N'-hexamethylenebis(4-carbamoyl-1-decylpyridinium bromide), N,N'-hexamethylenebis(4-carbamoyl-1-decylpyridinium acetate), 4,4'-(tetramethylenedicarbonyldiamino)bis(1-decylpyridinium bromide), 4,4'-(tetramethylenedicarbonyldiamino)bis(1-decylpyridinium acetate), 1,4-tetramethylenebis(4-carbamoyl-1-hexadecylpyridinium bromide), 1,6-hexamethylenebis(3-carbamoyl-1-dodecylpyridinium bromide), 1,8-octamethylenebis(3-carbamoyl-1-tetradecylpyridinium bromide), 3,3'-(1,3-trimethylenedicarbonyldiamino)bis(1-decyl-pyridinium bromide), 4,4'-(p-xylyldithio)bis(1-octylpyridinium iodide), 3,3'-(m-xylyldithio)bis(1-tetradecylpyridinium bromide), N, N'-(p-phenylene)bis(4-carbamoyl-1-octylpyridinium bromide), N,N'-(m-phenylene)bis(3-carbamoyl-1-dodecylpyridinium bromide), 4,4'-(p-phthalamido)bis(1-octylpyridinium bromide), 3,3'-(m-phthalamido)bis(1-octadecylpyridinium iodide), 4,4'-(1,8-octamethylenedioxy)bis(1-dodecylpyridinium bromide), 3,3'-(1,6-hexamethylenedioxy)bis(1-hexadecylpyridinium bromide), 4,4'-(1,6-hexamethylenedioxydicarbonyl)bis(1-octylpyridinium bromide), 3,3'-(1,4-tetramethylenedioxydicarbonyl)bis(1-dodecylpyridinium bromide), 4,4'-(1,4-tetramethylenedicarbonyldioxy)bis(1-octylpyridinium bromide), 3,3'-(p-phthaloyldioxy)bis(1-decylpyridinium chloride), 4,4'-(1,8-octamethylenedicarbonyldithioxy)bis(1-octadecylpyridinium bromide) and 3,3'-(m-phthaloyldithioxy)bis(1-decylpyridinium iodide).

4. The detergent composition of claim 1 comprising soap or another surfactant.

5. The detergent composition of claim 1 containing 0.1–50% by weight of the compound of the formula (I).

6. The detergent composition of claim 1 containing 1–20% by weight of the compound of the formula (1).

\* \* \* \* \*